United States Patent
Zhu (10) Patent No.: US 10,352,857 B2
(45) Date of Patent: Jul. 16, 2019

(54) USE OF PENTA-SUBSTITUTED TETRAHYDROPYRIMIDINES IN PREPARATION OF THERMO-SENSITIVE FLUORESCENT MATERIALS

(71) Applicant: SOUTHERN MEDICAL UNIVERSITY, Guangdong (CN)

(72) Inventor: Qiuhua Zhu, Guangdong (CN)

(73) Assignee: SOUTHERN MEDICAL UNIVERSITY, Guangdong (CN)

( * ) Notice: Subject to any disclaimer, the term of this patent is extended or adjusted under 35 U.S.C. 154(b) by 184 days.

(21) Appl. No.: 15/518,246

(22) PCT Filed: Apr. 5, 2016

(86) PCT No.: PCT/CN2016/078413
§ 371 (c)(1),
(2) Date: Apr. 11, 2017

(87) PCT Pub. No.: WO2016/173386
PCT Pub. Date: Nov. 3, 2016

(65) Prior Publication Data
US 2017/0307527 A1    Oct. 26, 2017

(30) Foreign Application Priority Data

Apr. 29, 2015  (CN) .......................... 2015 1 0212629

(51) Int. Cl.
| | | |
|---|---|---|
| *G01N 21/64* | (2006.01) | |
| *C07D 239/06* | (2006.01) | |
| *C09K 11/06* | (2006.01) | |
| *G01K 11/00* | (2006.01) | |
| *C09K 9/02* | (2006.01) | |
| *G01K 11/20* | (2006.01) | |

(52) U.S. Cl.
CPC ........... *G01N 21/64* (2013.01); *C07D 239/06* (2013.01); *C09K 9/02* (2013.01); *C09K 11/06* (2013.01); *G01K 11/00* (2013.01); *G01K 11/20* (2013.01)

(58) Field of Classification Search
None
See application file for complete search history.

(56) References Cited

U.S. PATENT DOCUMENTS

2014/0342390 A1   11/2014 Tsuji et al.

FOREIGN PATENT DOCUMENTS

| CN | 102250015 | 11/2011 |
| CN | 103113282 | 5/2013 |
| CN | 103113283 | 5/2013 |
| CN | 103411961 | 11/2013 |
| CN | 103483271 | 1/2014 |
| CN | 103755704 | 4/2014 |
| CN | 104845613 | 8/2015 |

OTHER PUBLICATIONS

P. R. N. Childs, et al., "Review of temperature measurement," Review of Scientific Instruments, vol. 71, No. 8, Aug. 2000, pp. 2959-2978.
Anat Bahat, et al., "Thermotaxis of mammalian sperm cells: A potential navigation mechanism in the female genital tract," Nature Medicine, vol. 9, No. 2, Feb. 2003, pp. 149-150.
Xu-Dong Wang, et al., "Luminescent probes and sensors for temperature," Chem. Soc. Rev., vol. 42, Jun. 24, 2013, pp. 7834-7869.
Kohki Okabe, et al., "Intracellular temperature mapping with a fluorescent polymeric thermometer and fluorescence lifetime imaging microscopy," Nature Communications, 3:705, Feb. 28, 2012, pp. 1-9.
Jiao Feng, et al., "A Triarylboron-Based Fluorescent Thermometer: Sensitive Over a Wide Temperature Range," Angew. Chem. Int. Ed., vol. 50, No. 35, Aug. 22, 2011, pp. 8072-8076.
Toshiki Mutai, et al., "Reproducible on-off switching of solid-state luminescence by controlling molecular packing through heat-mode interconversion," nature materials, vol. 4, Sep. 2005, pp. 685-687.
Xiqi Zhang, et al., "Multifunctional organic fluorescent materials derived from 9,10-distyrylanthracene with alkoxyl endgroups of various lengths," Chem. Commun., vol. 48, Sep. 18, 2012, pp. 10895-10897.
Quihua Zhu, et al., "A New Series of C-6 Unsubstituted Tetrahydropyrimidines: Convenient One-Pot Chemoselective Synthesis,Aggregation-Induced and Size-Independent Emission Characteristics," Chem. Eur. J., vol. 19, No. 4, Jan. 21, 2013, pp. 1268-1280.
Lan Huang, et al., "Copper-induced fluorescence enhancement and particle-size decrease of a C-6 unsubstituted tetrahydropyrimidine racemate," RSC Adv., vol. 3, No. 32, Jun. 2013, pp. 13286-13292.
"International Search Report (Form PCT/ISA/210) of PCT/CN2016/078413", dated Jul. 11, 2016, with English translation thereof, pp. 1-6.

*Primary Examiner* — Kamal A Saeed
(74) *Attorney, Agent, or Firm* — JCIPRNET (57) ABSTRACT

The present invention provides use of penta-substituted tetrahydropyrimidines in preparation of thermo-sensitive fluorescent materials. Said penta-substituted tetrahydropyrimidine compounds have linear temperature dependence of red-edge excitation wavelength (LTDREEW). When different excitation wavelengths are chosen, such compounds present fluorescence color and/or fluorescence on-off switch in different temperature ranges. Also their fluorescence intensity ratios or fluorescence intensities exhibit good linear relation or power function relation to temperature, which can be used as the thermo-sensitive fluorescent materials with high sensitivity and wide temperature range (0-450 K).

8 Claims, 8 Drawing Sheets

THP-1b

USE OF PENTA-SUBSTITUTED TETRAHYDROPYRIMIDINES IN PREPARATION OF THERMO-SENSITIVE FLUORESCENT MATERIALS

CROSS-REFERENCE TO RELATED APPLICATION

This application is a 371 application of an International PCT application serial no. PCT/CN2016/078413, filed on Apr. 5, 2016, which claims the priority benefits of China Application No. 201510212629.7, filed on Apr. 29, 2015. The entirety of each of the above-mentioned patent applications is hereby incorporated by reference herein and made a part of this specification.

TECHNICAL FIELD

The present invention relates to a technical field of thermo-sensitive organic luminescent materials, specifically disclosing the use of compounds with penta-substituted tetrahydropyrimidine structure in preparation of thermo-sensitive fluorescent materials.

BACKGROUND

Temperature is one of the most basic physical parameters influencing physical chemistry process and biological metabolism process. Thus, no matter in scientific research or in daily life, temperature detection is necessary, and temperature sensors accounts for 75-80% of worldwide market of sensors (*Review of Scientific Instruments* 2000, 71, 2959-2978). Temperature detection in different conditions or different research objects requires different temperature sensors. Along with the rapid development of disciplines and technologies such as molecular biology, proteomics, medical science and scientific instruments, multiple research fields have got in micro-dynamic detection process, for example the research of biological metabolism process and disease has extended to the process of molecule changes in biological cells (*Nature medicine* 2003, 9, 149-150). Such development has presented new challenge to temperature detection: real-time and remote detection of temperature and temperature distribution in a microenvironment. Traditional sensors detecting temperature by local contact, for example temperature sensor based on volume changes through thermal expansion and contraction of a substance, and thermocouple temperature indicator designed according to thermo-electric effect (Seebeck effect), can't fulfill the need of the development of these disciplines. In this aspect, fluorescent molecular or nano temperature sensors which have advantages such as ultrahigh sensitivity, extremely fast response speed, extremely high spatial resolution and safe remote detection, have attracted great attention (*Chemical Society Reviews* 2013, 42, 7834-7869).

Figure 1:
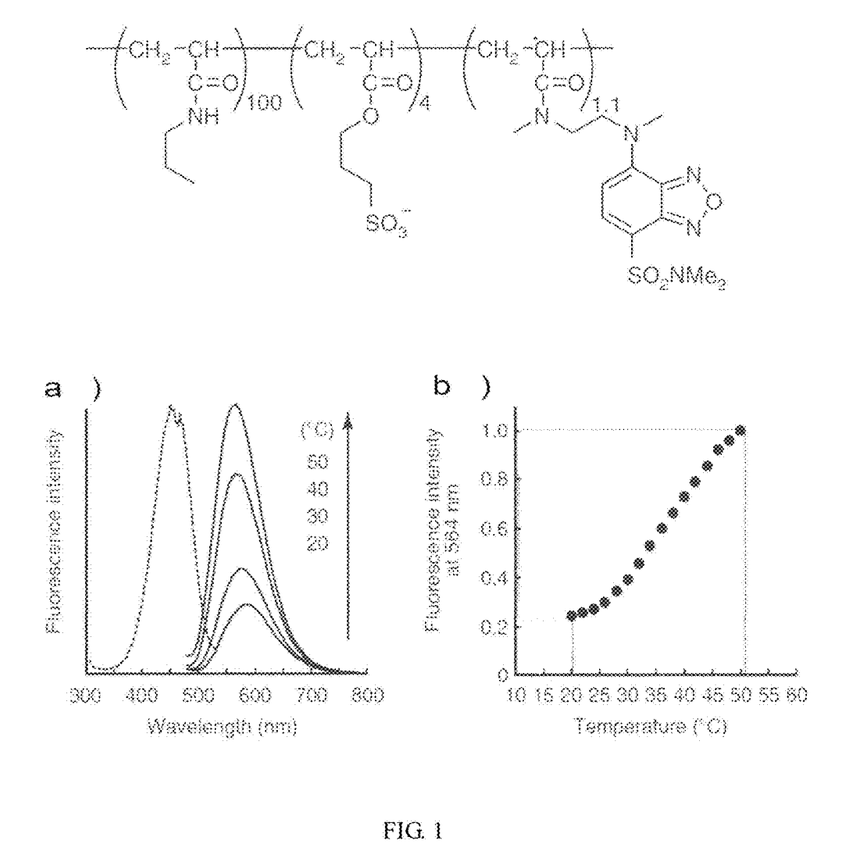
FIG. 1 shows an example of prior macromolecule organic compound 1 with thermo-sensitive fluorescent material. a) Excitation spectrum and emission spectrum of compound 1 along with temperature variation. b) Relation graph of fluorescence intensity of compound 1 at the emission spectrum peak value (564 nm) to temperature.

Theoretically, the fluorescence of all fluorescent compounds is related to temperature. This is because, on the one hand, temperature variation would bring the changes in the electronic energy level and electronic vibration level distribution of atoms or molecules, which thus would change the fluorescent property; on the other hand, temperature variation would bring change in the volume of compound, which would influence the interactions between atoms or between molecules and then change the fluorescent property. However, fluorescent compounds used as temperature probes are less because the compound serving as the temperature probe should satisfy the properties such as high sensitivity, good stability and reversibility (*Chemical Society Reviews* 2013, 42, 7834-7869). Nowadays, the reported thermo-sensitive fluorescent materials include macromolecular fluorescent compounds, small organic molecule fluorescent compounds, organometallic complexes, quantum dots, organic or inorganic nano materials, etc. (*Chemical Society Reviews* 2013, 42, 7834-7869). Some of fluorescent temperature probes have been used in intracellular temperature detection and imaging study, for example macromolecule compound 1 can be used in intracellular temperature imaging (*Nature communications* 2012, 3, 705) (FIG. 1).

Compared with inorganic and macromolecule fluorescent materials, the properties of small molecular organic fluorescent materials are relatively easy to be controlled owing to the following characteristics: (1) compounds with different optical properties can be easily obtained by structural modification; (2) material properties can be modified by oriented assembly in molecular level easily; (3) functional molecular structures can be changed on purpose to combine and integrate multiple functions.

Figure 2:
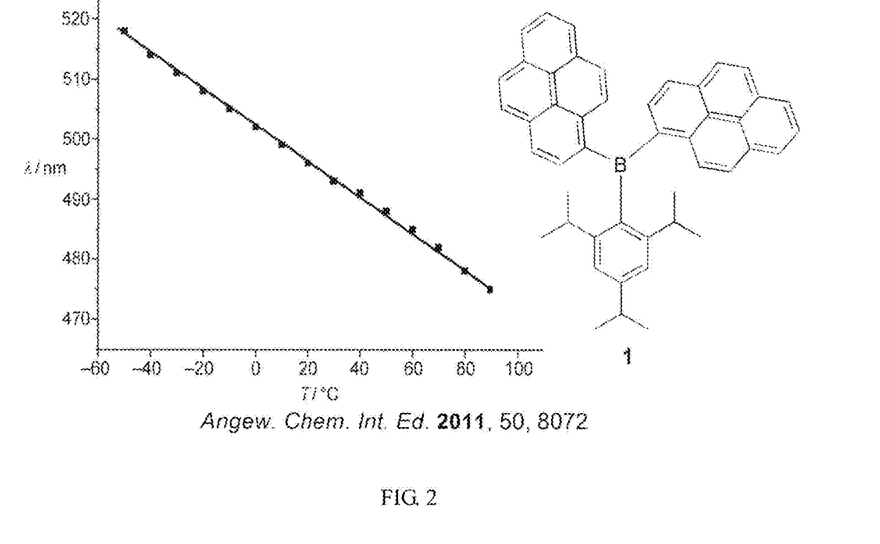
FIG. 2 shows the molecular structure of reported small organic molecule compound 2 with thermo-sensitive fluorescence and an example of linear relation graph of its emission wavelength in a polar solution to temperature.
Figure 3:
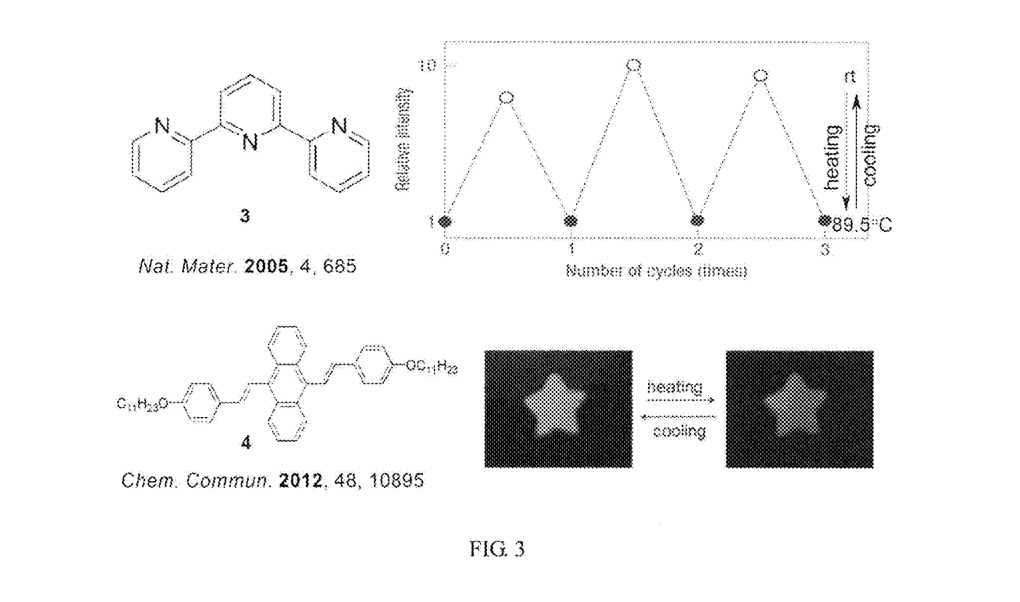
FIG. 3 shows the molecular structures of reported small organic molecule compounds 3 and 4 with thermo-sensitive fluorescence and an example of graph of solid fluorescence intensity or emission wavelength thereof reversibly varying with the temperature variation.

Besides, compared to temperature fluorescent probes of metallic quantum dots and metallic complexes, the temperature fluorescent probes of small molecular organic compounds are provided with less toxicity. But so far, fluorescent probes with high sensitivity and wide temperature range are metallic complex, quantum dot and organic polymer (*Chemical Society Reviews* 2013, 42, 7834-7869). Small molecular organic compounds that can be used as temperature probes are less, and most of them are molecular thermometers which are used in solutions and related to not only temperature but also solution polarity and pH value. For example, the fluorescence of compound 2 (FIG. 2) is related to not only temperature but also solution polarity, and it can only be used to detect temperature of solution with certain polarity. Thus, the temperature response of compound 2 was conducted in a polar solution of 2-methoxyethyl ether (FIG. 2) (*Angew. Chem. Int. Ed.* 2011, 50, 8072-8076). The application of such probe is limited, because the ideal temperature probe should be related to only temperature but not to other environmental factors. Environmental-responsive solid reversible fluorescent change has a more comprehensive application, but solid fluorescent compounds with reversible change by thermal stimulus are fairly less. As shown in FIG. 3, a fluorescence intensity of compound 3 (*Nat Mater* 2005, 4, 685-687), and the dual-color fluorescence of compound 4 (*Chemical Communications* 2012, 48, 10895-10897) display reversible change along with temperature. The solid-state fluorescence of organic compounds is related to not only molecular structures but also molecular stacking modes. The sensitive thermo-response of compounds 3 and 4 proves to be originated from the thermo-stimuli reversible change in molecular stacking modes.

The present inventor has disclosed penta-substituted tetrahydropyrimidines in CN201110129857.X, which have an aggregation-induced emission effect and can be used in organic electro-luminescence or photo-luminescence devices or chemical and biological fluorescent sensors and probes.

SUMMARY OF THE PRESENT INVENTION

An object of the present invention is to overcome the deficiencies of the prior art and provide use of penta-substituted tetrahydropyrimidines in preparation of thermo-sensitive fluorescent materials.

The above-described object of the present invention can be realized by the following technical solutions:

Use of penta-substituted tetrahydropyrimidines in preparation of thermo-sensitive fluorescent materials, wherein the penta-substituted tetrahydropyrimidines have structures shown as formula (I):

Wherein:

$R^1$ is selected from a group consisting of $C_{1-8}$ linear or branched alkyls and substituted $C_{1-8}$ alkyls;

$R^2$ and $R^4$ are independently selected from a group consisting of $C_{1-8}$ linear or branched alkyls, substituted $C_{1-8}$ alkyls, $C_{5-8}$ cycloalkyls, substituted $C_{5-8}$ cycloalkyls, $C_{5-6}$ aryls, substituted $C_{5-6}$ aryls, $C_{9-18}$ fused polycyclic aryls, substituted $C_{9-18}$ fused polycyclic aryls, $C_{5-6}$ heterocyclyls, substituted $C_{5-6}$ heterocyclyls, $C_{5-6}$ aromatic heterocyclyls and substituted $C_{5-6}$ aromatic heterocyclyls;

$R^3$ is selected from a group consisting of $C_{5-6}$ aryls, substituted $C_{5-6}$ aryls, $C_{9-18}$ fused polycyclic aryls, substituted $C_{9-18}$ fused polycyclic aryls, $C_{5-6}$ aromatic heterocyclyls and substituted $C_{5-6}$ aromatic heterocyclyls.

Preferably, the use of said penta-substituted tetrahydropyrimidines is in preparation of a chemical and/or biological fluorescent temperature sensors or probes.

After thorough research and analysis, the inventor has surprisingly discovered that penta-substituted tetrahydropyrimidines in CN201110129857.X not only has aggregation-induced emission effect, but also has linear temperature dependence of red-edge excitation wavelength (LTDREEW). Using the LTDREEW characteristics, such compounds can be used as temperature fluorescent probes with high sensitivity and wide temperature range, and their application range can be expanded. The LTDREEW characteristic is discovered for the first time. When different excitation wavelengths are chosen, these compounds can show mutation on fluorescence-color/or fluorescence-on-off switch in different temperature ranges from 0 K to their melting points. Their fluorescence intensity rates or fluorescence intensities exhibit a good linear relation or power function relation to temperature. When the temperature varies 35 K, the fluorescence intensity can vary by 10 times, and the sensitivity of fluorescence intensity to temperature is higher than that of the reported compound 1. Several of penta-substituted tetrahydropyrimidines have polymorphs and the fluorescence color of one of the polymorphs is particularly sensitive to temperature. When temperature varies 30 K, fluorescent wavelength varies 59 nm, and the sensitivity of fluorescent wavelength to temperature is higher than that of the reported compound 2. Besides, responsive temperature ranges of said penta-substituted tetrahydropyrimidines are far wider than those of the prior small molecular organic fluorescent compounds.

As a preferable embodiment, for the thermo-sensitive penta-substituted tetrahydropyrimidines, preferably $R^1$ is $C_{1-2}$ alkyls.

As a preferable embodiment, for the thermo-sensitive penta-substituted tetrahydropyrimidines, preferably $R^2$ is selected from a group consisting of $C_{1-5}$ linear or branched alkyls, substituted $C_{1-5}$ alkyls, $C_{5-8}$ cycloalkyls, $C_{5-6}$ aryls and substituted $C_{5-6}$ aryls.

As a preferable embodiment, for the thermo-sensitive penta-substituted tetrahydropyrimidines, preferably $R^3$ is $C_{5-6}$ aryls or substituted $C_{5-6}$ aryls.

As a preferable embodiment, for the thermo-sensitive penta-substituted tetrahydropyrimidines, preferably $R^4$ is selected from a group consisting of C s linear or branched alkyls, substituted $C_{1-5}$ alkyls, $C_{5-8}$ cycloalkyls, $C_{5-6}$ aryls and substituted $C_{5-6}$ aryls.

As a preferable embodiment, substituents are preferably selected from a group consisting of halogens, $C_{1-2}$ perhalogenated alkyls, $C_{1-4}$ halogenated alkyls, hydroxyl, $C_{1-6}$ linear or branched alkoxys, nitryl, cyano, amino, $C_{1-6}$ monoalkyl aminos, $C_{1-6}$ dialkyl aminos, $C_{5-8}$ monocycloalkyl aminos, $C_{5-6}$ monoheterocycloalkyl aminos, $C_{5-6}$ monoaryl aminos, $C_{1-6}$ alkyl acylaminos, $C_{5-6}$ aryl acylaminos, amino carbonyls, $C_{1-6}$ monoalkyl amino carbonyls, $C_{1-6}$ dialkyl amino carbonyls, $C_{1-6}$ alkyl acyls, $C_{5-8}$ aryl acyls, amino sulfones, $C_{1-6}$ monoalkyl amino sulfones, $C_{1-6}$ dialkyl amino sulfones, $C_{5-8}$ arylamino sulfones, $C_{1-6}$ alkyl sulfonyl aminos, carboxyl, $C_{1-6}$ monoalkyl sulfones, linear or branched alkyls, $C_{5-8}$ cycloalkyls, substituted $C_{5-8}$ cycloalkyls, $C_{2-4}$ alkenyls, $C_{2-4}$ alkynyls, aryl $C_{1-3}$ alkyls, $C_{5-6}$ aryls, substituted $C_{5-6}$ aryls, $C_{9-18}$ fused polycyclic aryls, $C_{5-6}$ heterocyclyls, $C_{5-6}$ aromatic heterocyclyls and $C_{9-18}$ fused polycyclic aromatic heterocyclyls.

As a preferable embodiment, for the thermo-sensitive material penta-substituted tetrahydropyrimidine, the following is preferable: in formula (I), $R^1$ is methyl or ethyl;

$R^2$ is selected from a group consisting of phenyl, methyl phenyl, chlorphenyl, bromophenyl, and trifluoromethyl phenyl, $R^3$ is selected from a group consisting of phenyl, bromophenyl, phenyl substituted by methoxy hydroxyl, bromophenyl, trifluoromethyl phenyl, naphthyl, and thienyl;

$R^4$ is selected from a group consisting of phenyl, methyl phenyl, chlorphenyl, bromophenyl, and trifluoromethyl phenyl.

Compared with the prior art, the present invention has the following beneficial effects:

The inventor has found that said penta-substituted tetrahydropyrimidine compound has linear temperature dependence of red-edge excitation wavelength (LTDREEW) characteristics. When choosing different excitation wavelength, it may present fluorescence color and/or fluorescence-on-off switch in different temperature range, in order to prepare sensitive thermo-sensitive fluorescent material; the thermo-sensitivity of said penta-substituted tetrahydropyrimidine compound is high (when temperature varies 30 K, emission wavelength varies 59 nm, and/or when temperature varies 35K, fluorescence intensity varies as 10 times.); and the detective temperature range of said penta-substituted tetrahydropyrimidine compound is wide (from 0K to 450K).

BRIEF DESCRIPTION OF THE DRAWINGS

FIG. 5 shows, in 77-300K detective range, the linear temperature dependence of red-edge excitation wavelength (LTDREEW) characteristics of THP-1g, as well as its characteristics of fluorescence-on-off switch and fluorescence linear relation to temperature in different temperature ranges; a) excitation spectrum varying with temperature (emission wavelength is 496 nm, and dotted line basically coincident with line with symbols is excitation spectrum detected in circulate temperature); b) linear relation graph of red-edge excitation wavelength to temperature (straight line with black square symbols), linear relation graph of fluorescence intensity at 496 nm in 90-210K range, which is excited at 420 nm, to temperature (straight line with circle symbols), and linear relation graph of fluorescence intensity at 496 nm in 180-300K range, which is excited at 438 nm, to temperature (straight line with pentagram symbols); c) excited at 420 nm, emission spectrum in 77-300K range; and d) excited at 438 nm, emission spectrum in 150-300K range;

FIG. 8 shows, in 90-300K detective range, the linear temperature dependence of red-edge excitation wavelength (LTDREEW) characteristics of THP-1b, as well as the characteristic of fluorescence-color and intensity-on-off switch in different temperature ranges when excited in different wavelength and linear relationship between fluorescence intensity and temperature. a) Excitation spectrums varying with temperature (lines with symbols are excitation spectrums where emission wavelength is 434 nm, while solid lines without symbols are excitation spectrums where emission wavelength is 510 nm, and the dotted lines basically coincident with the lines with symbols are excitation spectrums detected in circulate temperature); b) linear relation graph of red-edge excitation wavelengths at three different luminous intensity in FIG. 8a (three parallel lines in FIG. 8a) to temperature; c) excited at 365 nm, emission spectrum in 90-210K range; d) excited at 380 nm, emission spectrum in 90-300K range; and e) linear relation graph of fluorescence intensity at 433 nm in 90-210K range, which is excited at 365 nm, to temperature (straight line with square symbols), also linear relation graph of fluorescence intensity at 433 nm in 180-300K range, which is excited at 380 nm, to temperature (straight line with circle symbols);

DETAILED DESCRIPTION OF THE PREFERRED EMBODIMENT

The present invention is further described below in combination with specific embodiments which are not intended to limit the present invention in any manner. Unless otherwise specified, reagents and methods used in the embodiments are routinely used in this field of art.

Table 1 shows the molecular structures of compounds, maximum emission wavelength ($\lambda_{em}$), the ratio between fluorescence intensities at maximum emission wavelength at 80° C. and 20° C. ($I_{80}/I_{20}$), and melting points of the compounds in embodiments. Some of the compounds in the embodiments have been already disclosed in CN201110129857.X, and those compounds which have not been disclosed in CN201110129857.X specifically will be provided with relevant structural characteristic data herein.

Table 1 the molecular structures of compounds, maximum emission wavelength ($\lambda_{em}$), ratio between fluorescence intensities at maximum emission wavelength at 80° C. and 20° C. ($I_{80}/I_{20}$), and melting points of compounds in embodiments

| Compound number | $\lambda_{em}{}^a$/nm | $I_{80}/I_{20}{}^b$ | Melting point/° C. | Molecular structure |
|---|---|---|---|---|
| THP-1b | 434 | | 130.0-130.5 | |
| THP-1g | 484 | 0.85 | 119.5-120.0 |  |

-continued

| Compound number | $\lambda_{em}{}^a$/nm | $I_{80}/I_{20}{}^b$ | Melting point/°C. | Molecular structure |
|---|---|---|---|---|
| THP-2b | 469 | 0.57 | 149.0-149.5 | |
| THP-3 | 448 | 0.52 | 121.4-121.6 | |
| THP-4b | 445 | 0.43 | 136.5-137.0 | |
| THP-4g | 468 | 0.60 | 144.5-145.0 | |
| THP-4p | 425 | | 153.0-153.5 | |
| THP-5 | 451 | 0.93 | 152.3-153.0 | |

-continued

| Compound number | $\lambda_{em}{}^a$/nm | $I_{80}/I_{20}{}^b$ | Melting point/ °C | Molecular structure |
|---|---|---|---|---|
| THP-6 | 473 | 0.48 | 158.8-159.1 | |
| THP-7 | 477 | 0.80 | 145.3-146.2 | |
| THP-8 | 480 | 0.58 | 153.1-153.9 | |
| THP-9 | 458 | 0.80 | 196.2-196.4 | |

-continued

| Compound number | $\lambda_{em}{}^a$/nm | $I_{80}/I_{20}{}^b$ | Melting point/ °C | Molecular structure |
|---|---|---|---|---|
| THP-10 | 479 | 0.44 | 164.1-164.6 | |
| THP-11 | 490 | 0.76 | 164.1-164.6 | |
| THP-12 | 480 | 0.57 | 112.9-113.9 | |

$^a$Maximum emission wavelength; $^b$ratio between fluorescence intensity at maximum emission wavelength at 80° C. and fluorescence intensity at maximum emission wavelength at 20° C.

Figure 11:
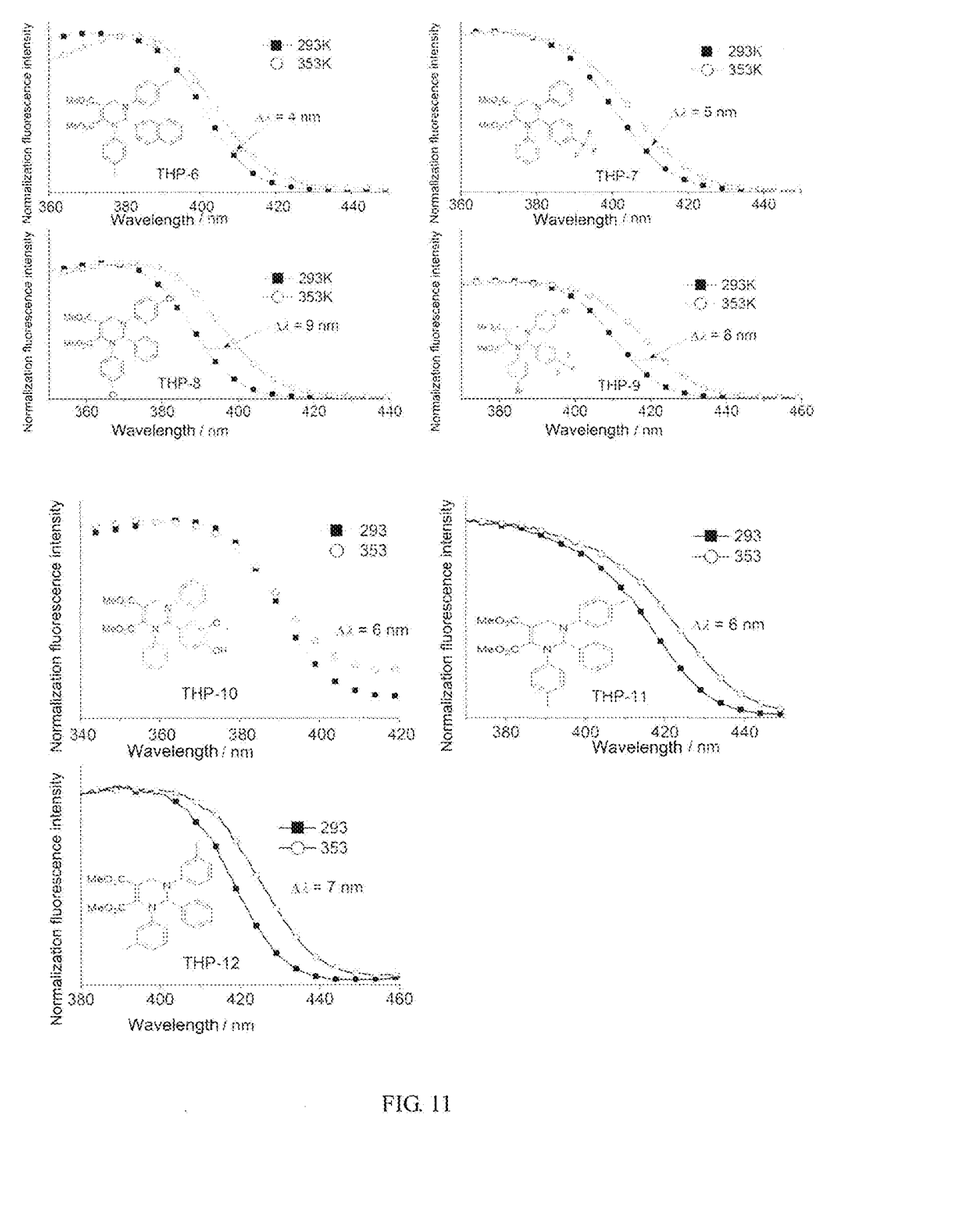
FIG. 11 shows, at 293K and 353K, the excitation spectrums of THP-1~12 which was emitted at maximum emission wavelength of each (with reference to Table 1) (THP-4b and THP-4g are polymorphs)
Figure 12:
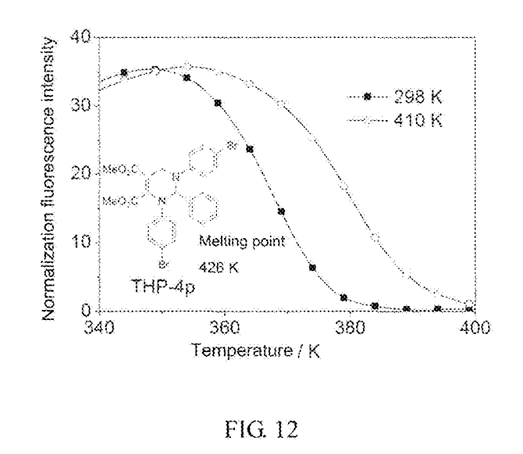
FIG. 12 shows, at 298K and 410K, the excitation spectrum of THP-4p (polymorph of THP-4b and THP-4g) which was emitted at its maximum emission wavelength (425 nm)

Wherein, compounds THP-1, THP-2, THP-5~8 and THP-10~12 were disclosed in the above-mentioned patent; compounds THP-4g, THP-4b and THP-4p were polymorphs separated from the known compounds, they having same molecular structure and same structural characteristic parameters, but the melting points and optical properties being different (the melting point and maximum emission wavelength of each are shown in Table 1, excitation spectrums are shown in FIG. 11 and FIG. 12); and compounds THP-3 and THP-9 are new compounds of which synthetic methods may refer to the prior art with choosing relevant raw material, with properties as well as structural characteristic data thereof being as follows:

THP-3 Dimethyl 1,2,3,6-tetrahydro-1,3-diphenyl-2-(thiophen-2-yl)pyrimidine-4,5-dicarboxylate 35% yield, yellow solid, mp=121.4-121.6° C.; IR (KBr): $v_{max}$=2949, 1742, 1702, 1593, 1495, 1241, 1110, 1064, 976, 843, 752, 696 cm$^{-1}$; $^1$H NMR (400 MHz, CDCl$_3$) h=7.47-7.02 (m, 13H), 6.30 (s, 1H), 4.33 (d, J=17.6 Hz, 1H), 3.88 (d, J=17.6 Hz, 1H), 3.72 (s, 3H), 3.66 (s, 3H) ppm; $^{13}$C NMR (101 MHz, CDCl$_3$) δ=165.71, 164.69, 148.49, 144.23, 143.91, 142.15, 129.32, 129.21, 127.08, 126.60, 126.46, 126.28, 124.18, 121.87, 119.06, 102.03, 52.52, 51.49, 42.65 ppm; MS (ESI): m/z 435 (M+H$^+$, 27), 248 (100); Anal. Calcd for C$_{24}$H$_{22}$N$_2$O$_4$S: C, 66.34; H, 5.10; N, 6.45. Found: C, 66.53; H, 5.10; N, 6.61.

THP-9 Dimethyl 1,3-bis(4-bromophenyl)-2-(4-(trifluoromethyl)phenyl)-1,2,3,6-tetrahydropyrimidine-4,5-dicarboxylate 24% yield, white solid, mp=196.2-196.4° C.; IR (KBr): vmax=2951, 2303, 1740, 1704, 1606, 1489, 1325, 1241, 1114, 893, 748 cm-1; 1H NMR (400 MHz, CDCl3) δ=7.76-6.73 (m, 12H), 6.04 (s, 1H), 4.24 (d, J=18.4 Hz, 1H), 3.72 (s, 3H), 3.69 (s, 3H), 3.53 (d, J=18.4 Hz, 1H) ppm; 13C NMR (101 MHz, CDCl3) δ=165.21, 164.33, 148.06, 143.06, 141.45, 132.55, 132.37, 127.28, 126.30, 125.05, 120.69, 119.75, 114.53, 103.19, 79.53, 52.83, 51.68, 42.66 ppm; MS (ESI): m/z 653 (M+H+, 27), 655 (M+H+, 53), 326 (100); Anal. Calcd for C27H21Br2F3N2O4: C, 49.57; H, 3.24; N, 4.28. Found: C, 49.58; H, 3.29; N, 4.17.

Embodiment 1

Figure 4:
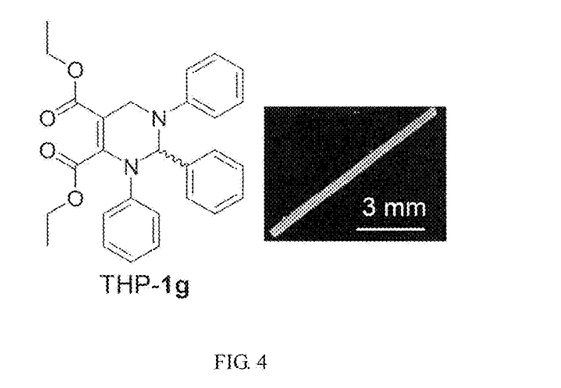
FIG. 4 shows the molecular structure of said penta-substituted tetrahydropyrimidine THP-1 according to the present invention and the photograph of its polymorph crystal THP-1g with green emitting (emission wavelength is 496 nm)
Figure 5:
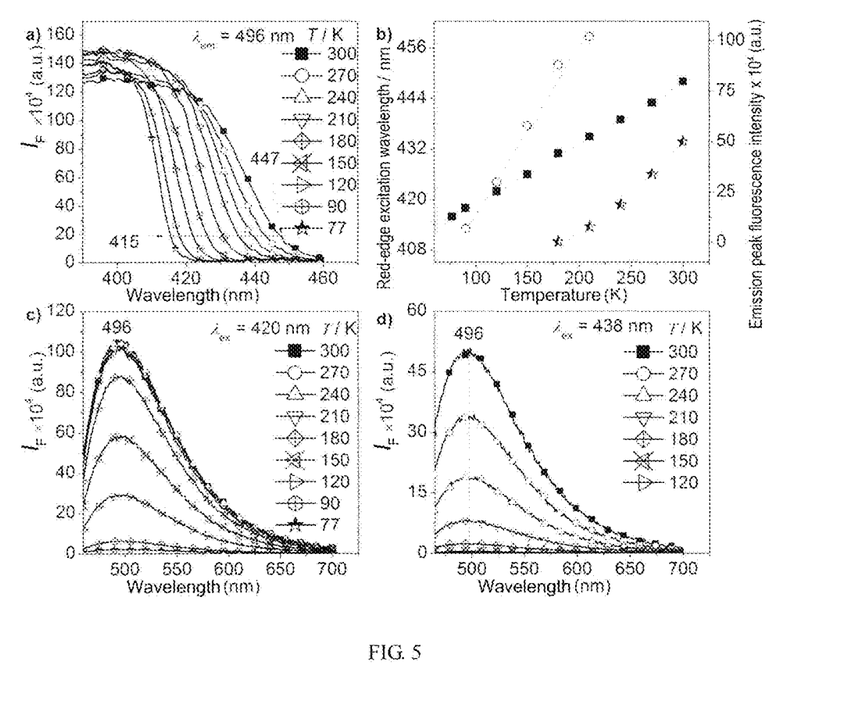

(1) From 300 to 77K, the excitation spectra emitted at maximum emission wavelength by a low-temperature luminoscope (seeing FIG. 5a), and emission spectra excited at two different red-edge excitation wavelengths (FIG. 5c and FIG. 5d) of penta-substituted tetrahydropyrimidine THP-1 (molecular structure and crystal graph are shown in FIG. 4) were detected using by a low-temperature luminoscope. From FIG. 5a and FIG. 5b, it can be seen that red-edge excitation wavelength/fluorescence intensity exhibits good linear relation to temperature, i.e. with linear temperature dependence of red-edge excitation wavelength (LTDREEW) characteristics. From FIGS. 5c, 5d and 5b, it can be seen that fluorescence intensity exhibits good linear relation to temperature in detective temperature range if suitable excitation wavelength is chosen.

(2) Temperature from 300 to 90K may be detected precisely by sensitive fluorescence-on-off change of THP-1g by choosing suitable excitation wavelength using LTDREEW characteristics.

Figure 6:
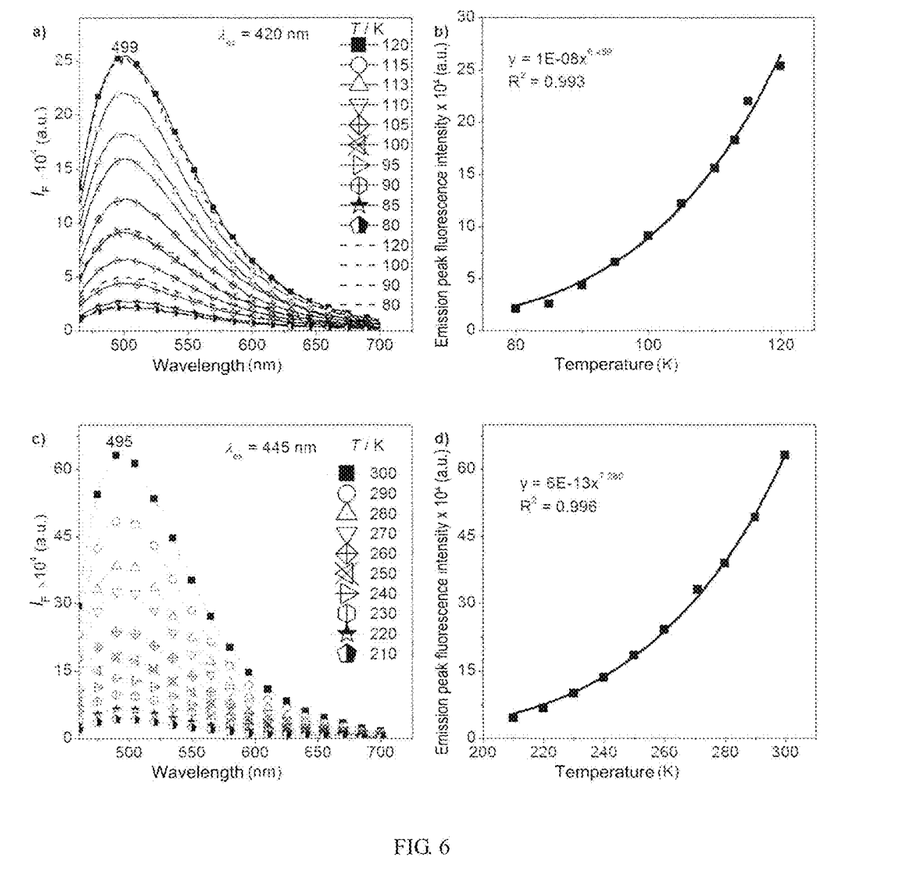
FIG. 6 shows temperature variation in different ranges precisely detected based on the characteristic of fluorescence-on-off switch in different temperature ranges when excited at different wavelengths. Wherein a) and b) respectively show when THP-1g was excited at 420 nm, emission spectrum in 80-120K range and the power function linear relation graph of emission peak fluorescence intensity to temperature; c) and d) respectively show when THP-1g was excited at 445 nm, emission spectrum in 210-300K range and the power function linear relation graph of emission peak fluorescence intensity to temperature.

Example 1, temperature from 80 to 120K was detected precisely at 420 nm excitation wavelength by the low-temperature luminoscope. As shown in FIG. 6a, when temperature varied 35K, fluorescence intensity of THP-1g varied as 10 times. At the same time, it can be seen from FIG. 6b that, fluorescence intensity exhibited good power function relation to temperature, and temperature from 80 to 120K can be detected precisely and sensitively.

Example 2, temperature from 300 to 210K was detected precisely at 445 nm excitation wavelength by the low-temperature luminoscope. As shown in FIG. 6c, when temperature varied 90K, fluorescence intensity of THP-1g varied as 14 times. At the same time, it can be seen from FIG. 6d that, fluorescence intensity exhibited good power function relation to temperature, and temperature from 300 to 210K can be detected precisely and sensitively.

Embodiment 2

Figure 7:
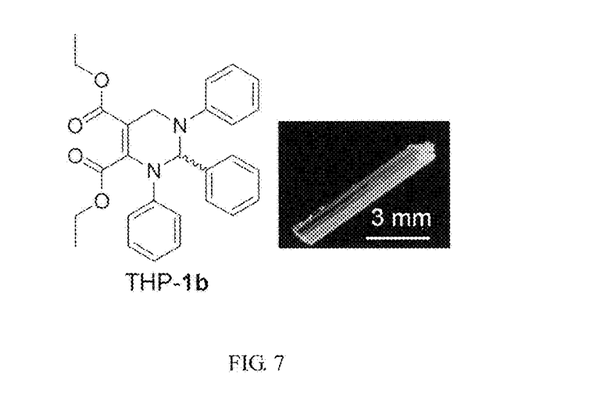
FIG. 7 shows the molecular structure of said penta-substituted tetrahydropyrimidine THP-1 according to the present invention and the photograph of its polymorph crystal THP-1b with blue emitting (emission wavelength is 433 nm)
Figure 8:
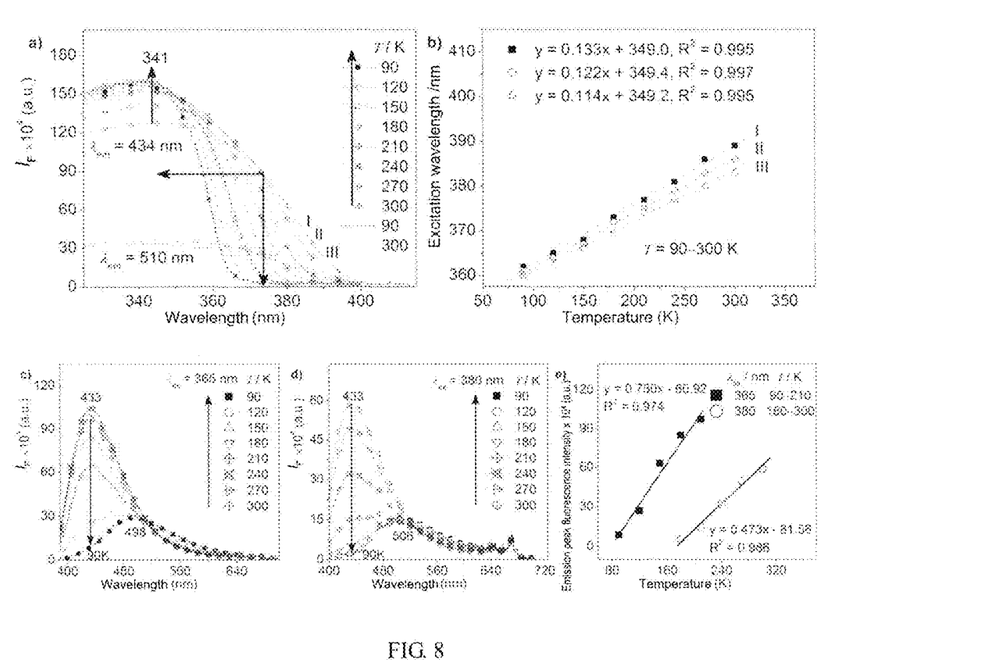

(1) Every 30K from 300 to 90K, the excitation spectra emitted at the maximum emission wavelengths of two fluorescence components with short wavelength and long wavelengths, respectively (seeing FIG. 8a), emission spectra excited at two different red-edge excitation wavelengths (FIG. 8c and FIG. 8d) of the polymorph emitting blue fluorescence (THP-1b) of penta-substituted tetrahydropyrimidine THP-1 (crystal graph is shown in FIG. 7) by a low-temperature luminoscope. From FIG. 8a and FIG. 8b, it can be seen that red-edge excitation wavelength exhibits good linear relation to temperature, i.e. with linear temperature dependence of red-edge excitation wavelength (LTDREEW) characteristics. From FIGS. 8c, 8d and 8e, it can be seen that good linear relation can be obtained in detective temperature range if suitable excitation wavelength was chosen.

(2) Temperature from 0K to melting point of THP-1b can be detected precisely by choosing suitable excitation wavelength using the characteristics of LTDREEW and dual-color fluorescence of THP-1b.

Figure 9:
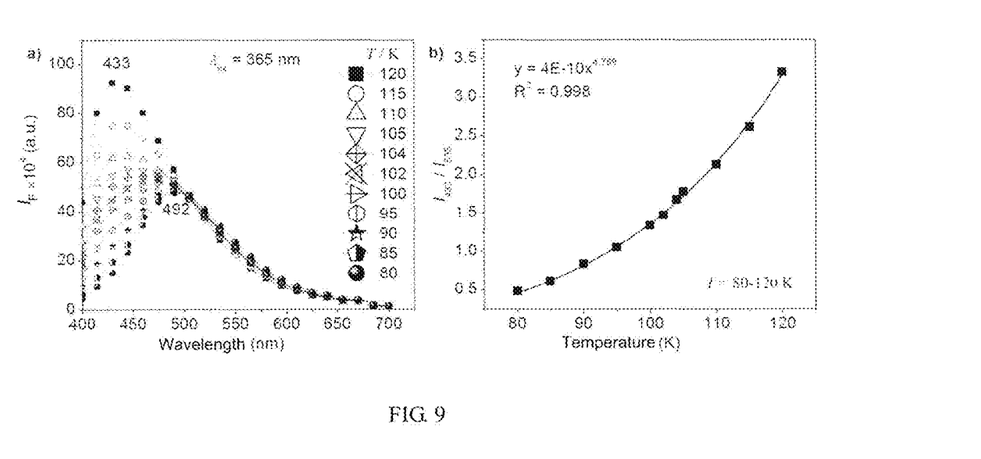
FIG. 9 shows temperature variation in different ranges precisely detected based on the characteristics of the fluorescence color and intensity-on-off switches of THP-1b in different temperature ranges when excited at different wavelengths. a) Emission spectrum in 80-120K range when THI-1b was excited at 365 nm; b) power function relation graph of fluorescence intensity ratio at 433 nm and 535 nm to temperature.

Example 1, temperature from 120 to 80K can be detected precisely by the low-temperature luminoscope choosing 365 nm excitation wavelength. From FIG. 9a, it can be seen that when temperature varied 30K (from 110 to 80K), maximum emission wavelength varied 59 nm (from 433 to 492 nm). That is, fluorescence component transformed from basically short wavelength fluorescence component to basically long wavelength fluorescence component, and such fluorescence component transformation, i.e. fluorescence color change, can be observed directly by naked eyes. Meanwhile, as shown in FIG. 9b, the fluorescence-intensity ratio of the two fluorescent components of THP-1b exhibits great power function relation to temperature.

Figure 10:
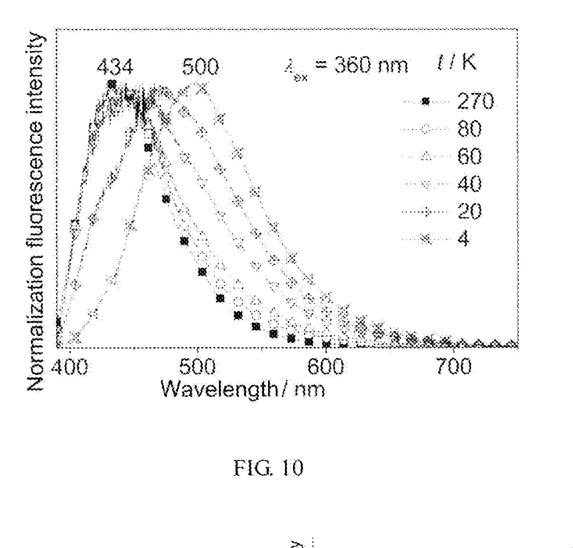
FIG. 10 shows the emission spectrum of THP-1b in 4-298K range, which was excited at 360 nm excitation wavelength.

Example 2, temperature from 4 to 80K can be detected precisely by low-temperature luminoscope choosing 360 nm excitation wavelength. From FIG. 10, it can be seen that when temperature varied 56K (from 60 to 4K), maximum emission wavelength varied 66 nm (from 434 to 500 nm). That is, fluorescence component transformed from main fluorescence component with short wavelength to main fluorescence component with long wavelength, and such fluorescence component transformation, i.e. fluorescence color change, can be observed directly by naked eyes.

Embodiment 3

The excitation spectra of twelve penta-substituted tetrahydropyrimidines THP-1~12 and a general fluorescent probe pyrene for detecting critical micelle concentration of surfactants were detected at 20° C. and 80° C. by using a general luminoscope with a temperature regulating device (the molecular structures of compounds, maximum emission wavelength ($\lambda_{em}$), ratio between fluorescence intensities at maximum emission wavelength at 80° C. and 20° C. ($I_{80}/I_{20}$), and melting points of compounds are shown in Table 1), in order to determine whether the compound has LTDREEW characteristics or not and to determine the sensitive level that the red-edge excitation wavelength shows to temperature. That is, whether red-edge excitation wavelength is influenced by temperature or not and what level the red-edge excitation wavelength is influenced by temperature can determine whether the compound has LTDREEW characteristics or not and the sensitive level that the red-edge excitation wavelength shows to temperature. As shown in FIG. 11, red-edge excitation wavelengths of twelve penta-substituted tetrahydropyrimidines (THP-1~12, wherein THP-4g and THP-4b are polymorphs) are all influenced by temperature, i.e. they all have LTDREEW characteristics, but the red-edge excitation wavelengths were influenced by temperature on different levels. Some red-edge excitation wavelength difference value ($\Delta\lambda$) is 9 nm, while some red-edge excitation wavelength difference value ($\Delta\lambda$) is only 4 nm. Thus, all detective penta-substituted tetrahydropyrimidines can be used for fluorescent thermal detection or fluorescent thermal imaging analysis like THP-1.

Embodiment 4

The excitation spectra of THP-4p (polymorph of THP-4g and THP-4g) (molecular structure of compound, maximum emission wavelength ($\lambda_m$) and melting point of compound are shown in Table 1) were detected at 298K and 410 k by a low-temperature luminoscope. As shown in FIG. 12, when THP-4p is close to its melting point (153° C., i.e. 426K), the red-edge excitation wavelength of THP-4p still varied with temperature, i.e. it still had LTDREEW characteristics, wherein the ratio between fluorescence intensities at maximum emission wavelength at 410K and 298K was 0.68. This embodiment indicates that red-edge excitation wavelength of THPs from 0K to melting point thereof all have sensitive response to temperature, and they have relatively strong fluorescence intensity when close to the melting point.

Embodiment 5

Figure 13:
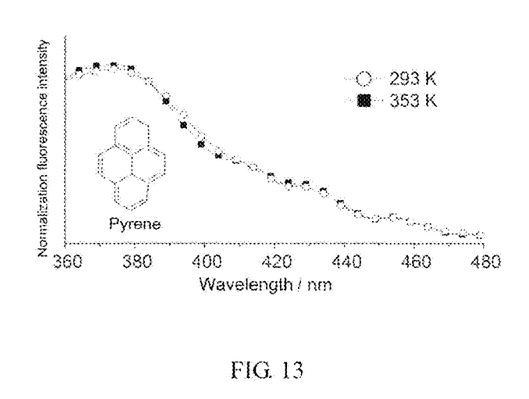
FIG. 13 shows, at 293K and 353K, the excitation spectrum of pyrene which was emitted at its maximum emission wavelength (496 nm).

Excitation spectra of general fluorescent compound pyrene at 20° C. and 80° C. were detected using a general luminoscope with a temperature regulating device. As shown in FIG. 13, it can be seen that the red-edge excitation wavelengths of pyrene are not influenced by temperature, i.e. pyrene does not have LTDREEW characteristics, and it indicates that not all fluorescent compounds have LTDREEW characteristics.

What is claimed:

1. A method of using penta-substituted tetrahydropyrimidines as temperature fluorescent sensors or probes, the method comprises:

providing fluorescent sensors or probes containing penta-substituted tetrahydropyrimidines, said penta-substituted tetrahydropyrimidines have structures shown as formula (I):

wherein:
$R^1$ is selected from a group consisting of $C_{1-8}$ linear or branched alkyls and substituted $C_{1-8}$ alkyls;
$R^2$ and $R^4$ are independently selected from a group consisting of $C_{1-8}$ linear or branched alkyls, substituted $C_{1-8}$ alkyls, $C_{5-8}$ cycloalkyls, substituted $C_{5-8}$ cycloalkyls, $C_{5-6}$ aryls, substituted $C_{5-6}$ aryls, $C_{9-18}$ fused polycyclic aryls, substituted $C_{9-18}$ fused polycyclic aryls, $C_{5-6}$ heterocyclyls, substituted $C_{5-6}$ heterocyclyls, $C_{5-6}$ aromatic heterocyclyls and substituted $C_{5-6}$ aromatic heterocyclyls;
$R^3$ is selected from a group of $C_{5-6}$ aryls, substituted $C_{5-6}$ aryls, $C_{9-18}$ fused polycyclic aryls, substituted $C_{9-18}$ fused polycyclic aryls, $C_{5-6}$ aromatic heterocyclyls and substituted $C_{5-6}$ aromatic heterocyclyls; and
detecting a change in temperature based on a linear or power function relationship between fluorescence intensity ratios or fluorescence intensities of the fluorescence sensors or probes and temperature, and tuning fluorescence-response temperature range by changing excitation wavelengths based on a linear temperature dependence of red-edge excitation wavelength (LTDREEW) characteristics of said penta-substituted tetrahydropyrimidines.

2. The method of claim 1, wherein the fluorescent sensors or probes are chemical and/or biological temperature fluorescent sensors or probes containing said penta-substituted tetrahydropyrimidines.

3. The method of claim 1, wherein $R^1$ is $C_{1-2}$ alkyls.

4. The method of claim 1, wherein $R^2$ is selected from a group consisting of $C_{1-5}$ linear or branched alkyls, substituted $C_{1-5}$ alkyls, $C_{5-8}$ cycloalkyls, $C_{5-6}$ aryls and substituted $C_{5-6}$ aryls.

5. The method of claim 1, wherein $R^3$ is $C_{5-6}$ aryls or substituted $C_{5-6}$ aryls.

6. The method of claim 1, wherein $R^4$ is selected from a group consisting of $C_{1-5}$ linear or branched alkyls, substituted $C_{1-5}$ alkyls, $C_{5-8}$ cycloalkyls, $C_{5-6}$ aryls and substituted $C_{5-6}$ aryls.

7. The method of claim 1, wherein substituents are selected from a group consisting of halogens, $C_{1-2}$ perhalogenated alkyls, $C_{1-4}$ halogenated alkyls, hydroxyl, $C_{1-6}$ linear or branched alkoxys, nitryl, cyano, amino, $C_{1-6}$ monoalkyl aminos, $C_{1-6}$ dialkyl aminos, $C_{5-8}$ monocycloalkyl aminos, $C_{5-6}$ monoheterocycloalkyl aminos, $C_{5-6}$ monoaryl aminos, $C_{1-6}$ alkyl acylaminos, $C_{5-6}$ aryl acylaminos, amino carbonyls, $C_{1-6}$ monoalkyl amino carbonyls, $C_{1-6}$ dialkyl amino carbonyls, $C_{1-6}$ alkyl acyls, $C_{5-8}$ aryl acyls, amino sulfones, $C_{1-6}$ monoalkyl amino sulfones, $C_{1-6}$ dialkyl amino sulfones, $C_{5-8}$ arylamino sulfones, $C_{1-6}$ alkyl sulfonyl aminos, carboxyl, $C_{1-6}$ monoalkyl sulfones, linear or branched alkyls, $C_{5-8}$ cycloalkyls, substituted $C_{5-8}$ cycloalkyls, $C_{2-4}$ alkenyls, $C_{2-4}$ alkynyls, aryl $C_{1-3}$ alkyls, $C_{5-6}$ aryls, substituted $C_{5-6}$ aryls, $C_{9-18}$ fused polycyclic aryls, $C_{5-6}$ heterocyclyls, $C_{5-6}$ aromatic heterocyclyls and $C_{9-18}$ fused polycyclic aromatic heterocyclyls.

8. The method of claim 1, wherein,
$R^1$ is methyl or ethyl;
$R^2$ is selected from a group consisting of phenyl, methyl phenyl, chlorphenyl, bromophenyl, and trifluoromethyl phenyl,
$R^3$ is selected from a group consisting of phenyl, bromophenyl, phenyl substituted by methoxy hydroxyl, bromophenyl, trifluoromethyl phenyl, naphthyl, and thienyl;
$R^4$ is selected from a group consisting of phenyl, methyl phenyl, chlorphenyl, bromophenyl, and trifluoromethyl phenyl.

* * * * *